June 8, 1937. H. A. VERSCHUREN Plant Pat. 249
ROSE
Filed Nov. 6, 1936
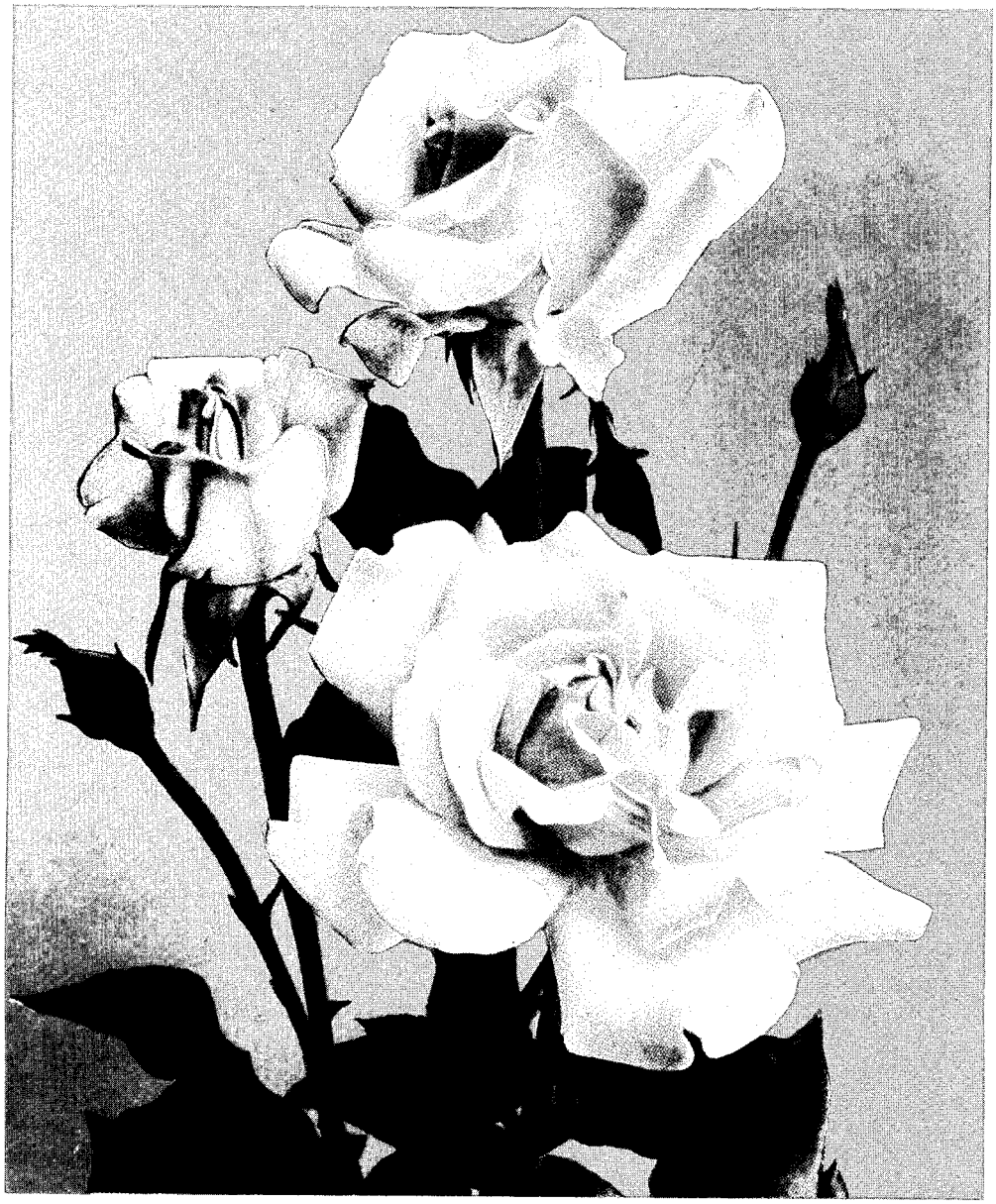
INVENTOR
Hendrikus Antonie Verschuren
By Orville M. Kile
Plant Patent Agent Patented June 8, 1937

Plant Pat. 249

UNITED STATES PATENT OFFICE

249

ROSE

Hendrikus Antonie Verschuren, near Uden, Netherlands, assignor to Henry A. Dreer, Incorporated, Philadelphia, Pa., a corporation of New Jersey Application November 6, 1936, Serial No. 109,591

1 Claim. (Cl. 47—61)

The present invention relates to a new and distinct variety of rose plant of the hybrid tea class, it being the result of definite breeding efforts to produce a rose of a distinct color and vigorous growth. This result was accomplished by a cross between the Mrs. Sam McGredy, seed parent, and Briarcliff.

This variety is of the greenhouse forcing type although it can also be grown as a garden rose.

The original illustrations accompanying this application show in full color a partially opened bud and two flowers in different stages of opening, two buds not yet showing color, together with stems and foliage.

Following is a detailed description of the rose and all color references are to Ridgway's Color Standards and Nomenclature.

*The flower*

Bud:—

*Peduncle.*—Medium to long; strong; reddish in color; covered with very fine spines.

*Color.*—Inner petals of opening bud are Grenadine (Plate II). Outer petals Grenadine Pink (Plate II) with Deep Chrome (Plate III) covering large portion at base of each petal.

*Shape.*—Urn-shaped.

Bloom:—

*Size.*—Large, 5 inches across.

*Petalage.*—Double, from 35 to 40 petals in the month of June.

*Form.*—Open, usually retaining closed and somewhat pointed center.

Petals:—

*Substance.*—Thick.

*Veining.*—Rather prominent.

*Shape.*—Outer petals oval; slightly inclined to roll backward.

*Fragrance.*—Mildly fragrant.

*Behavior.*—Drop off cleanly.

*Color.*—Edges are Begonia Rose (Plate I) with Orange Buff (Pl. III) beginning at the base and suffusing into the Rose color. Many petals have a streak of the Orange Buff extending the entire vertical length of the petal.

*General color effect.*—Light Salmon Orange (Plate II) with a suffusion of Geranium Pink (Plate I), and a rich sheen of silvery rose, which is not in the Color Standards. In fact, the entire color tone of this new rose is so distinct that a new color has been named after it—"Queen Mary." The tips of the petals fade first, changing to lighter pinks. Chrome yellow at base of petals is notable in the open flower, due to the opening of outer four or five rows of petals and retention of the closed center, leaving some space between in which the Chrome color stands out promiently. This effect persists even in advanced stages.

*Reproductive organs*

*Stamens.*—Very large number (together with pistils they fill the entire center of flower). Arranged in circle about pistils.

*Filaments.*—Irregular in length; yellow.

*Anthers.*—Large; yellow; all open at once.

*Pollen.*—Scarce.

*Pistils.*—Very many; closely bunched.

*Styles.*—Red; uneven; short.

*Stigma.*—Light yellow.

*Ovaries.*—Wholly inclosed in calyx.

*Hips.*—Medium; walls thick; green.

*Sepals.*—Moderately recurved; wide; short; only very slightly foliaceous.

*The bush*

Foliage:—Inclined to be sparse.

*Leaves.*—Compound; 3 to 5 leaflets. Occasionally a single leaf occurs. Quite small, usually 1 to 1½ inches long. Leathery; tendency to curl and not lie in flat plane.

*Leaflets.*—Oval with acute apex; edge moderately serrate; wavy.

*Color.*—Upper side Yew Green (Plate XXXI), under side Hellebore Green (Plate XVII).

*Rachis.*—Medium; smooth with occasional small thorn on under side.

*Stipules.*—Long; pointed; narrow.

*Stems.*—Stiff; strong.

*Color.*—Yellowish Olive (Plate XXX).

*Thorns.*—Notably plentiful; reddish brown; large; sharp, almost horizontal but pointing slightly downward.

*Blooming habit.*—Very free bloomer.

*Growth.*—Vigorous and strong. Bush, somewhat spreading.

*Disease resistance.*—Exceedingly healthy.

Among the most notable and distinguishing features of this new variety of rose are (1) the novel color of its blossoms, (2) the habit of opening which retains a closed and somewhat pointed center (3) the small size of the leaflets, (4) the large number of stiff, sharp thorns on the flower stems, and (5) the short, smooth and practically non-branching sepals.

Having thus disclosed my invention, I claim:

A new and distinct variety of rose plant as shown and described, characterized particularly by the distinctive new coloring of its buds and flowers.

HENDRIKUS ANTONIE VERSCHUREN.